(12) United States Patent
Matsumoto et al.

(10) Patent No.: US 11,571,542 B2
(45) Date of Patent: Feb. 7, 2023

(54) MOBILE TERMINAL, FRAGRANCE GENERATION DEVICE, SERVER, FRAGRANCE DETERMINATION METHOD, AND PROGRAM

(71) Applicant: SHISEIDO COMPANY, LTD., Tokyo (JP)

(72) Inventors: Kaoru Matsumoto, Kanagawa (JP); Yuka Nago, Tokyo (JP); Masaki Hanahara, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 586 days.

(21) Appl. No.: 16/491,853

(22) PCT Filed: Mar. 9, 2017

(86) PCT No.: PCT/JP2017/009527
§ 371 (c)(1),
(2) Date: Sep. 6, 2019

(87) PCT Pub. No.: WO2018/163361
PCT Pub. Date: Sep. 13, 2018

(65) Prior Publication Data
US 2021/0128868 A1    May 6, 2021

(51) Int. Cl.
*A61M 21/02* (2006.01)
*H04M 1/21* (2006.01)
(Continued)

(52) U.S. Cl.
CPC .............. *A61M 21/02* (2013.01); *A61L 9/14* (2013.01); *G16H 20/70* (2018.01); *G16H 40/63* (2018.01);
(Continued)

(58) Field of Classification Search
CPC ...... A61M 2205/3303; A61M 15/0003; A61M 2230/10; A61M 2205/587;
(Continued)

(56) References Cited

U.S. PATENT DOCUMENTS

2013/0190556 A1* 7/2013 Wetmore .............. A61M 21/02
600/28

FOREIGN PATENT DOCUMENTS

| JP | 2002-282231 A | 10/2002 |
| JP | 2002-288348 A | 10/2002 |

(Continued)

OTHER PUBLICATIONS

Suki na Kaori de Kibun UP! Sumaho de Jizai ni Chogo Dekiru Smart Hokozai, [online], Kabushiki Kaisha WILBY, Jan. 26, 2017, [retrieval date Mar. 24, 2017, Internet:<URL: http://sakidori.co/article/169759>.

(Continued)

*Primary Examiner* — Christine H Matthews
*Assistant Examiner* — Joshua Daryl D Lannu
(74) *Attorney, Agent, or Firm* — Morgan, Lewis & Bockius LLP

(57) ABSTRACT

A fragrance suitable for a user can be provided. A mobile terminal includes: an acquisition unit that acquires a psychosomatic state from a physiological index of a user; an input unit that inputs future information of the user; a determination unit that determines a recipe including one or more types and a mixing ratio of one or more perfumes based on the psychosomatic state and the future information; and a communication unit that transmits the recipe to a fragrance generation device.

18 Claims, 10 Drawing Sheets

(51) Int. Cl.
    *A61L 9/14*     (2006.01)
    *G16H 40/63*     (2018.01)
    *G16H 20/70*     (2018.01)
    *A61B 5/16*     (2006.01)
    *A61M 21/00*     (2006.01)

(52) U.S. Cl.
CPC ............... *H04M 1/21* (2013.01); *A61B 5/163* (2017.08); *A61B 5/165* (2013.01); *A61L 2209/11* (2013.01); *A61L 2209/134* (2013.01); *A61M 2021/0016* (2013.01); *A61M 2021/0077* (2013.01); *A61M 2205/3303* (2013.01); *A61M 2205/3306* (2013.01); *A61M 2205/3569* (2013.01); *A61M 2205/3584* (2013.01); *A61M 2205/502* (2013.01); *A61M 2205/505* (2013.01); *A61M 2230/04* (2013.01); *A61M 2230/63* (2013.01)

(58) Field of Classification Search
CPC ...... A61M 2021/0016; A61M 2205/52; A61M 2205/3553; A61M 21/02; A61M 2021/0077; A61M 2205/502; A61M 2230/63; A61M 11/005; A61M 2021/0027; A61M 2205/8206; A61M 2230/04; A61M 2230/65; A61M 2021/0044; A61M 2205/505; A61M 2205/3006; A61M 2205/3569; A61M 2205/3592; A61M 2230/50; A61M 2205/3375; A61M 2205/07; A61M 2205/3584; A61M 2230/40; A61M 2230/005; A61L 9/14; A61L 2209/134; A61L 9/122; A61L 2209/11; A61L 2209/135; A61L 2209/12; A61L 2209/111; A61L 9/125; A61L 2209/132; H04M 1/21; H04M 1/72403; H04M 19/04; G16H 20/13; G16H 50/20; G16H 40/63; G16H 20/70; A61B 5/1103; A61B 5/7475; A61B 2503/12; A61B 5/165; A61B 5/0033; A61B 5/024; A61B 5/0816; A61B 5/4848; A61B 5/0077; A61B 5/163; A61B 5/1128; G06F 2203/001

See application file for complete search history.

(56) References Cited

FOREIGN PATENT DOCUMENTS

| | | | | |
|---|---|---|---|---|
| JP | 2002288348 | A | * | 10/2002 |
| JP | 2003-038630 | A | | 2/2003 |
| JP | 2003038630 | A | * | 2/2003 |
| JP | 2016-097208 | A | | 5/2016 |
| JP | 2016097208 | A | * | 5/2016 |
| JP | 2016-214495 | A | | 12/2016 |

OTHER PUBLICATIONS

International Search Report (with partial translation) and Written Opinion issued in corresponding International application No. PCT/JP2017/009527, dated Apr. 4, 2017.

* cited by examiner

| PLANNED ACTION | NOTE |
|---|---|
| WORK, STUDY | A' |
| EXERCISE | B' |
| HOUSEWORK, OTHER | C' |
| DRESSING | D' |
| AT EASE | E' |
| SLEEP | F' |

MOBILE TERMINAL, FRAGRANCE GENERATION DEVICE, SERVER, FRAGRANCE DETERMINATION METHOD, AND PROGRAM

TECHNICAL FIELD

The present invention relates to a mobile terminal, a fragrance generation device, a server, a fragrance determination method, and a program.

BACKGROUND ART

A technology of switching a state of mind and body by using a fragrance is known. Patent Literature 1 discloses a technology of evaluating biometrics information of a subject in aroma therapy, calculating the degree of conformableness or the degree of relaxation, and feeding back the type and the concentration of a perfume suitable for the subject. Patent Literature 2 discloses a technology of atomizing, at a short distance from a user, a dilute solution in which a perfume component is diluted based on a predetermined condition.

CITATION LIST

Patent Literature

PTL 1: Japanese Patent Application Laid-Open No. 2002-282231
PTL 2: Japanese Patent Application Laid-Open No. 2016-214495

SUMMARY OF INVENTION

Technical Problem

In the technologies disclosed in Patent Literatures 1 and 2, it is possible to provide a fragrance to the user based on a physiological index such as brain waves, heartbeats, or the like. However, it is not always easy to provide a suitable fragrance based on only the physiological index.

In view of such problems, the present invention intends to provide a mobile terminal, a fragrance generation device, a server, a fragrance determination method, and a program that can provide a suitable fragrance to a user.

Solution to Problem

A mobile terminal according to the present invention includes: an acquisition unit that acquires a psychosomatic state from a physiological index of a user; an input unit that inputs a planned action of the user; a determination unit that determines a recipe including one or more types and a mixing ratio of one or more perfumes based on the psychosomatic state and the planned action; and a communication unit that transmits the recipe to a fragrance generation device.

A fragrance determination method according to the present invention includes steps of: acquiring a psychosomatic state from a physiological index of a user; inputting a planned action of the user; and determining a recipe including one or more types and a mixing ratio of one or more perfumes based on the psychosomatic state and the planned action.

Advantageous Effects of Invention

According to the present invention, a mobile terminal, a fragrance generation device, a server, a fragrance determination method, and a program that can provide a suitable fragrance to a user are provided.

DESCRIPTION OF EMBODIMENTS

First Embodiment

Figure 1:
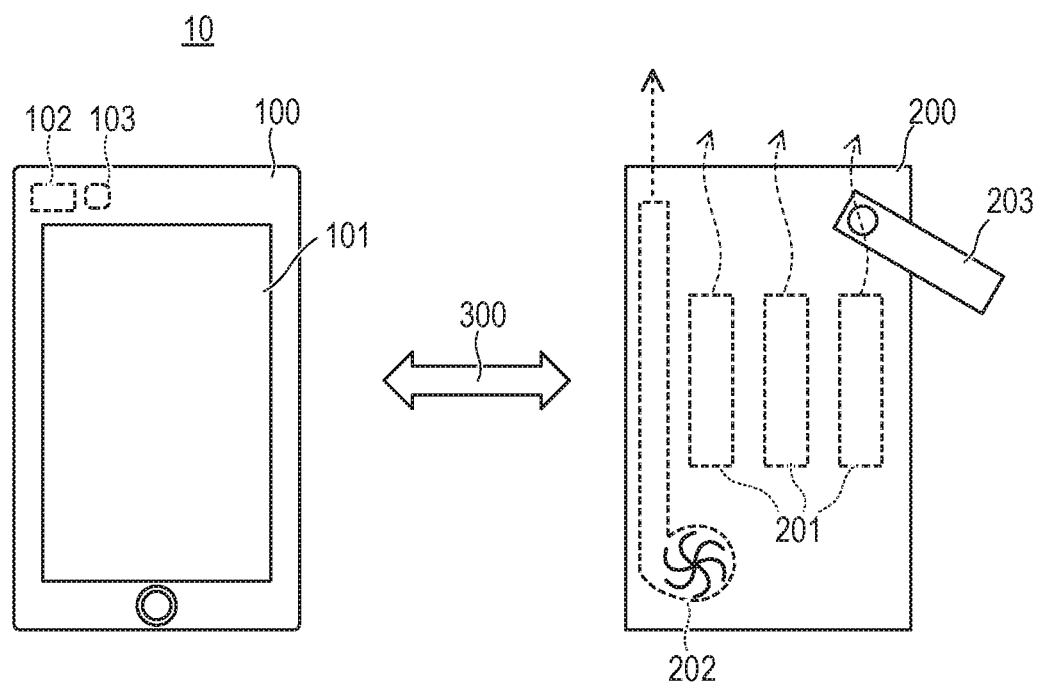
FIG. 1 is a schematic diagram of a fragrance generation system according to a first embodiment.

FIG. 1 is a schematic diagram of a fragrance generation system 10 according to the present embodiment. The fragrance generation system 10 has a mobile terminal 100 and a fragrance generation device 200. The mobile terminal 100 and the fragrance generation device 200 are connected to each other via a wireless communication 300 by Bluetooth (registered trademark). The mobile terminal 100 may be, for example, an information terminal such as a smartphone, a tablet computer, a Personal Digital Assistant (PDA), a laptop computer, a mobile phone, or the like. A smartphone will be illustrated below as an example of the mobile terminal 100. Note that the wireless communication 300 is not limited to Bluetooth (registered trademark), any communication scheme can be used which is capable of direct communication without via a network, such as Near Field Communication (NFC), infrared communication, a wireless LAN in an ad-hoc mode.

A touchscreen 101 is provided on the front face of the mobile terminal 100, and an image capture unit (camera) 102 and a light emitting diode (LED) 103 are provided on the upper part of the back face. The LED 103 is arranged near the image capture unit 102 and can be used as a flash light when capturing is performed by the image capture unit 102. In the mobile terminal 100, an application program for determining a fragrance recipe (hereafter, referred to as a fragrance determination app) is pre-installed. The fragrance determination app may be downloaded from a network (not illustrated) or may be supplied to the mobile terminal 100 through a storage medium such as a memory card.

An icon of the fragrance determination app is displayed on the touchscreen 101, and the fragrance determination app starts up in response to the user touching on the icon. Once the user slightly presses its fingertip on the image capture unit 102, the fragrance determination app performs capturing for a predetermined period and acquires heartbeat information on the user. Further, a user interface provided by the fragrance determination app is displayed on the touchscreen 101, the user selects a current mood and a planned action from displayed choices. The fragrance determination app can determine a fragrance recipe suitable for the user based on these pieces of information, that is, heartbeat information, the current mood, and the planned action. The determined fragrance recipe is displayed on the touchscreen 101 and transmitted to the fragrance generation device 200 via the wireless communication 300.

The fragrance generation device 200 has a cylindrical casing and includes a plurality of perfume cartridges 201 and a fan 202 inside the casing. The fragrance generation device 200 atomizes a perfume based on a fragrance recipe received via the wireless communication 300. A handle 203 is provided on the side face of the fragrance generation device 200, and the user may easily carry the fragrance generation device 200. The user may change the installation place of the fragrance generation device 200 in accordance with a living scene, such as in a living room, a study, a bedroom, or the like, for example.

Each of the perfume cartridges 201 is formed in a cylindrical shape and contains a liquid perfume in which a solid or liquid perfume is solved in an organic solvent. The perfume cartridge 201 is removable from the fragrance generation device 200, and the user may easily perform replacement. An ultrasonic vibrator (illustrated) is provided to the perfume cartridge 201, and the perfume is atomized by vibration of the ultrasonic vibrator.

The fan 202 is provided in the bottom of the fragrance generation device 200 and generates an airflow upward. A flow path is formed along the inner wall of the fragrance generation device 200 above the fan 202, and the air taken by the fan 202 is exhausted from the upper part of the fragrance generation device 200 through the flow path. An opening for emitting the perfume is provided in the upper face of the perfume cartridge 201, and the atomized perfume is carried on the airflow and diffused around from the opening.

Figure 2:
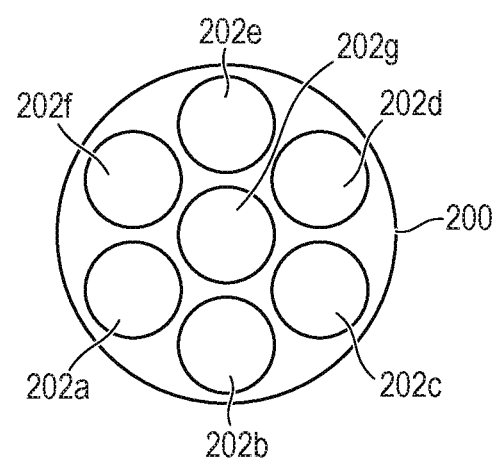
FIG. 2 is one example of the arrangement of perfume cartridges according to the first embodiment.

Note that different types of perfumes are contained in the perfume cartridges 201, and the number of cartridges provided in the fragrance generation device 200 is not particularly limited. Further, water instead of a perfume may be contained in the perfume cartridge 201. FIG. 2 illustrates one example of the arrangement of the perfume cartridges 201.

FIG. 2 is a schematic diagram of the fragrance generation device 200 when viewed from the upper side, and seven perfume cartridges 201a to 201g are provided in the fragrance generation device 200. Water is contained in the center perfume cartridge 201g, and different types of perfumes are contained in the six perfume cartridges 201a to 201f arranged around the perfume cartridge 201g, respectively. By atomizing water from the perfume cartridge 201g and adjusting the humidity around the fragrance generation device 200, it is possible to change the easiness of diffusion of a perfume or the strength of a fragrance felt by the user.

Figure 3:
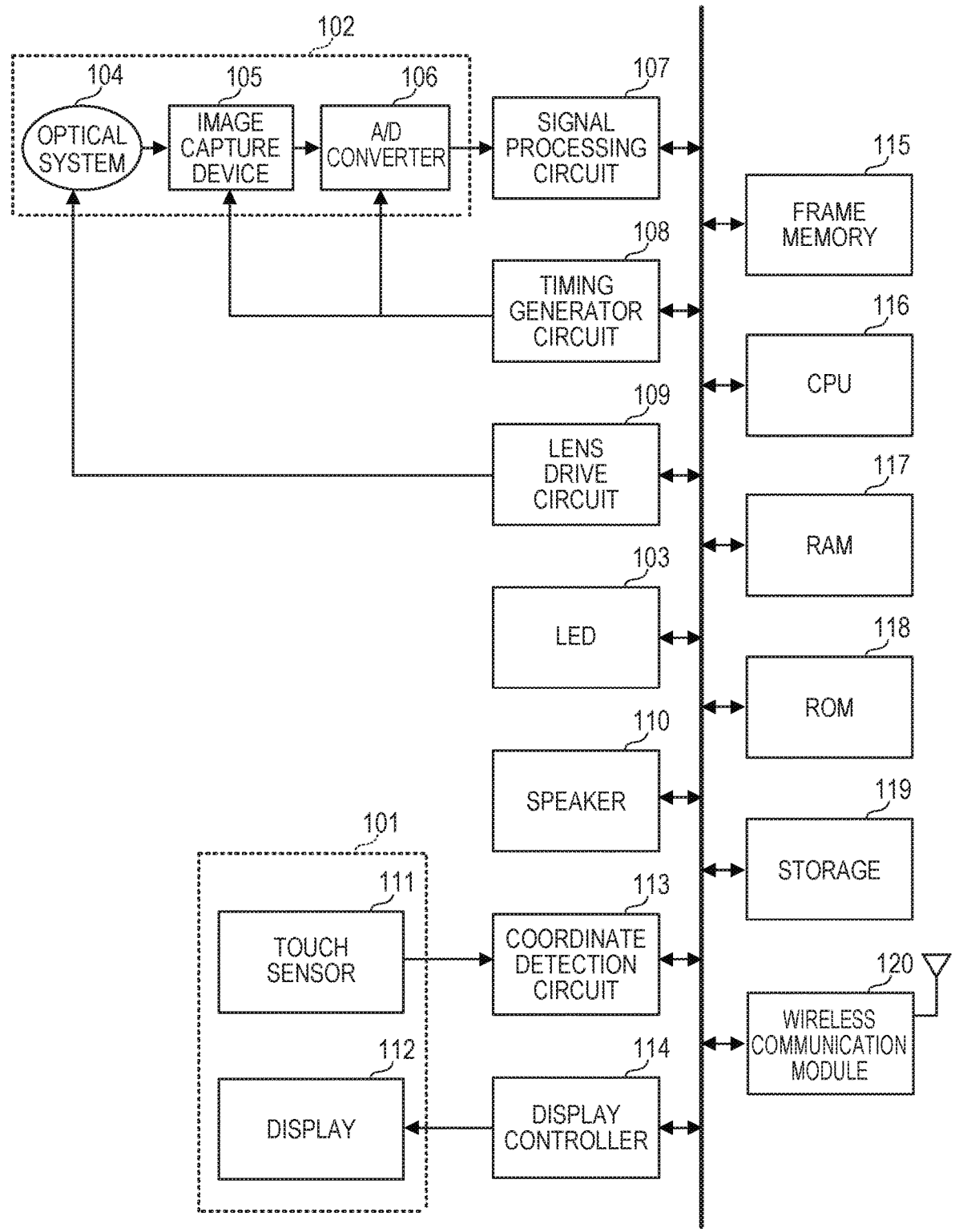
FIG. 3 is a block diagram of a mobile terminal according to the first embodiment.

FIG. 3 is a block diagram of the mobile terminal 100 according to the present embodiment. The mobile terminal 100 has the image capture unit 102, the LED 103, a signal processing circuit 107, a timing generation circuit 108, a lens drive circuit 109, a speaker 110, a touch sensor 111, a display 112, a coordinate detection circuit 113, and a display controller 114. The mobile terminal 100 further has a frame memory 115, a central processing unit (CPU) 116, a random access memory (RAM) 117, a read only memory (ROM) 118, a storage 119, and a wireless communication module 120.

The image capture unit 102 is formed of an optical system 104, an image capture device 105, and an analog/digital (A/D) converter 106. The optical system 104 includes an optical filter, a fixed lens, and a focus lens and captures a light from a subject (capturing position) onto an image capture surface of the image capture device 105 to form a subject image. The image capture device 105 is a Complementary Metal Oxide Semiconductor (CMOS) image sensor or a Charge Coupled Device (CCD) image sensor, for example, and has a plurality of two-dimensionally arranged pixels, color filters, and micro-lenses. The plurality of pixels may include pixels used for image capturing and pixels used for focus detection. Further, the image capture device 105 has an electronic shutter function that controls a charge accumulation period. Each of the plurality of pixels outputs a pixel signal based on an incident light from the optical system 104.

The A/D converter 106 is formed of a comparator circuit, a latch circuit, or the like and converts an analog pixel signal from the image capture device 105 into digital image data. The A/D converter 106 may be provided inside the image capture device 105. The timing generation circuit 108 generates a drive signal including a horizontal synchronization signal and a vertical synchronization signal and outputs the drive signal to the image capture device 105 or the A/D converter 106. The image capture unit 102 can output a moving image of a predetermined framerate in addition to a static image. The framerate may be any value such as $\frac{1}{4}$ seconds, $\frac{1}{30}$ seconds, $\frac{1}{60}$ seconds, or the like, for example, and is preferably $\frac{1}{60}$ seconds or less (for example, $\frac{1}{120}$ seconds or the like) in order to perform heartbeat measurement at high accuracy.

The signal processing circuit 107 includes a numeral calculation circuit and can perform digital signal processing such as white balance adjustment, gamma correction, pixel interpolation, contour emphasis, gradation conversion, noise reduction, compression, or the like on image data from the A/D converter 106. The lens drive circuit 109 has an actuator and can drive the focus lens of the optical system 104 and adjust a focus distance. The timing generation circuit 108 outputs timing signals such as a clock signal, a synchronization signal, or the like to the image capture device 105 or the A/D converter 106.

The LED 103 is a light source provided near the optical system 104 and emits a light to a capturing position in order to obtain an illuminance suitable for image capturing. The speaker 110 has a piezoelectric vibration unit and a reproduction circuit and is used for outputting a music, a message, a sound effect, or the like in addition to a voice call.

The touch sensor 111 is a capacitive sensor having transparent matrix electrodes and is provided on the display 112. In response to a finger of the user touching on the touch sensor 111, the static capacitance in the electrodes changes. The coordinate detection circuit 113 can detect a change in the static capacitance in the touch sensor 111 and calculate a position on which the finger of the user touches. The touch sensor 111 is used for accepting an instruction from the user.

The display 112 is a Thin Film Transistor (TFT) liquid crystal display or an organic Electro Luminescence (EL) display, for example, and displays an image, a moving image, a text, an icon, or the like in accordance with a display signal from the display controller 114. Further, the display 112 displays a user interface provided by the fragrance determination app. The display controller 114 is a processor including a video memory and controls display of the display 112. The display controller 114 temporarily stores display data from the CPU 116 and generates and outputs a display signal to the display 112. The touch sensor 111 and the display 112 are formed integrally to form the touchscreen 101.

The frame memory 115 can temporarily hold image data of multiple frames and may be used in image processing performed by the signal processing circuit 107 or the CPU 116. For example, CPU 116 performs heartbeat measurement by detecting, from image data of multiple frames, a change in a color component of a fingertip due to a change in a blood flow. Note that a part of the RAM 117 may be used as the frame memory 115. The CPU 116 has a CPU core, a cache memory or the like and integrally controls respective units of the mobile terminal 100. The CPU 116 can implement control of the mobile terminal 100 by reading and executing a predetermined program from the RAM 118 or the storage 119.

The RAM 117 is a dynamic RAM (DRAM), for example, and is used for a work region of the CPU 116, a load region of a program, or the like. The ROM 118 is an electrically erasable programmable ROM (EEPROM), for example, and stores Basic Input Output System (BIOS), various setting files, or the like. The storage 119 is a flash memory, for example, and stores a basic program such as Operating System (OS), various application programs such as the fragrance determination app, and a recipe file described later. The storage 119 may store image data obtained by the image capture unit 102, a measurement result obtained by the fragrance determination app, or the like.

The wireless communication module 120 is an interface for performing wireless communication with an external device. The wireless communication module 120 has an antenna and a transceiver circuit and can establish connection to an external device by using a communication scheme such as Bluetooth (registered trademark), a wireless LAN, or the like. For example, connection to an external device is possible up to a distance around 10 meters in radius by using communication by Bluetooth (registered trademark), for example. The wireless communication module 120 configures a communication unit and is used for transmitting and receiving data to and from the fragrance generation device 200.

Figure 4:
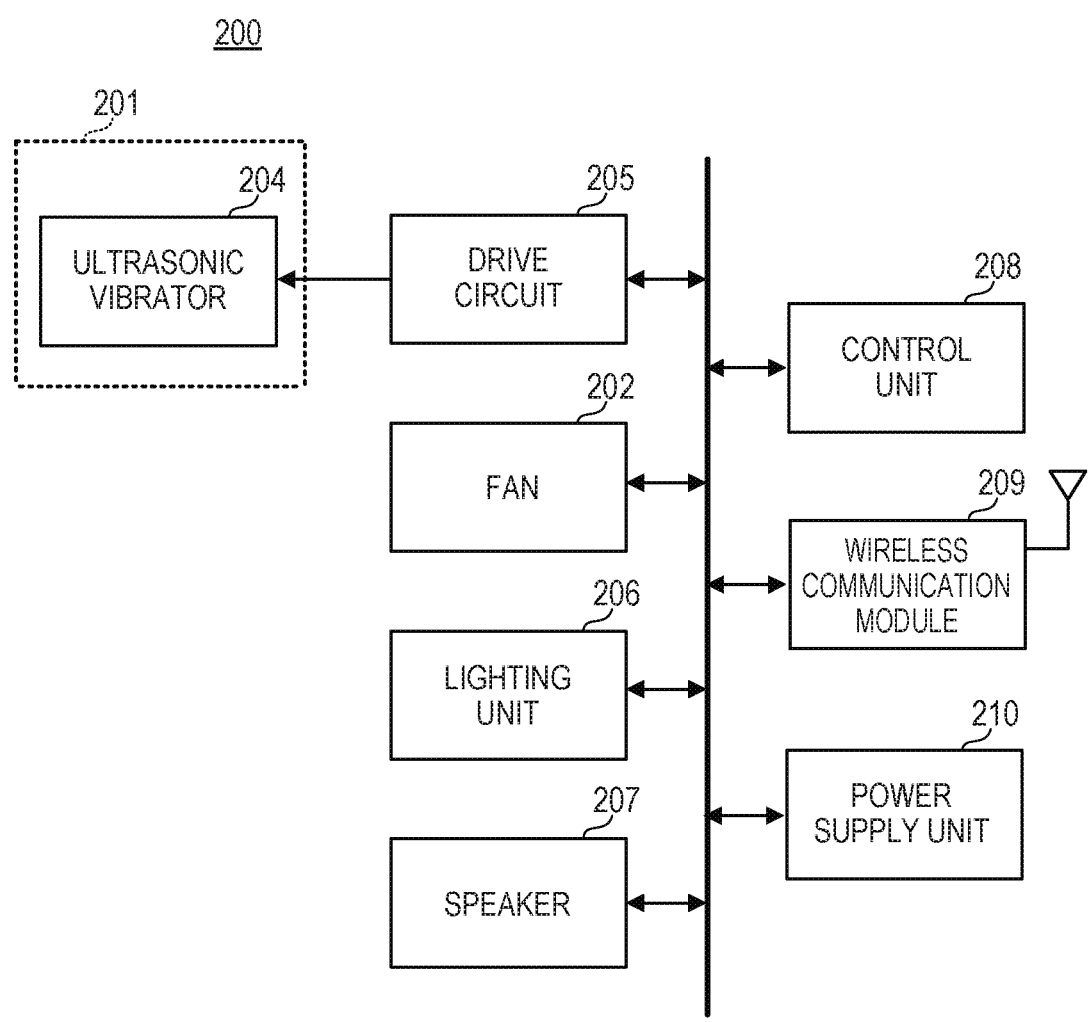
FIG. 4 is a block diagram of a fragrance generation device according to the first embodiment.

FIG. 4 is a block diagram of the fragrance generation device 200 according to the present embodiment. The fragrance generation device 200 has the perfume cartridge 201, the fan 202, an ultrasonic vibrator 204, a drive circuit 205, a lighting unit 206, a speaker 207, a control unit 208, a wireless communication module 209, and a power supply unit 210.

The ultrasonic vibrator 204 is built in the perfume cartridge 201 and connected to the drive circuit 205 via a connection cord. The ultrasonic vibrator 204 has a plate-shape piezoelectric ceramics and electrodes formed on both faces thereof and repeats expansion and contraction in response to being applied with a high frequency voltage from the drive circuit 205 to generate ultrasonic vibration. The ultrasonic vibration enables the perfume contained in the perfume cartridge 201 to be atomized. Note that, although depiction is omitted, a plurality of ultrasonic vibrators 204 are connected to the fragrance generation device 200, and the drive circuit 205 can drive the plurality of ultrasonic vibrators 204, independently.

The drive circuit 205 converts power from the power supply unit 210 to generate a high frequency voltage at the resonance frequency of the ultrasonic vibrator 204. The drive circuit 205 applies a high frequency voltage to the ultrasonic vibrator 204 based on a signal from the control unit 208. The fan 202 has an impeller and a motor unit and can send out an air. That is, the motor unit rotates the impeller based on a signal from the control unit 208, and the impeller generates an airflow.

The lighting unit 206 is formed of a plurality of LEDs and provided inside the casing of the fragrance generation device 200. The lighting unit 206 can control the intensity, the color tone, or the blinking pattern of a light based on a signal from the control unit 208 and, with a part of the casing being transparent or semitransparent, is used as indirect lighting or illumination. The speaker 207 has a piezoelectric vibration unit and a reproduction circuit and, for example, is used for outputting a music or a natural sound (a wave sound, a birdcall, or the like) having a relaxation effect or an effect of increasing concentration as a background music (BGM).

The control unit 208 has a CPU, a memory, an interface, and the like and integrally controls respective units of the fragrance generation device 200. The control unit 208 can implement control of the fragrance generation device 200 by reading and executing a predetermined program from the memory. For example, the control unit 208 can control the operation timing of the drive circuit 205 or the fan 202 based on a fragrance recipe received from the mobile terminal 100.

The wireless communication module 209 is an interface used for wireless communicating with an external device. The wireless communication module 209 has an antenna and a transceiver circuit and can establish connection to an external device by using a communication scheme such as Bluetooth (registered trademark), a wireless LAN, or the like. For example, connection to an external device is possible up to a distance around 10 meters in radius by using communication by Bluetooth (registered trademark). The wireless communication module 209 is used for transmitting and receiving data to and from the mobile terminal 100.

The power supply unit 210 has a battery, a Direct Current (DC)-DC converter, and a regulator circuit. The battery is a lithium ion rechargeable battery, a nickel hydrogen rechargeable battery, or an alkaline battery, for example, and outputs a DC power. The DC-DC converter and the regulator circuit convert the power of the battery and supply the converted power to each unit of the fragrance generation device 200. Note that the battery may be configured to be charged from an external power supply via a USB terminal or may be configured to be charged by contactless wireless powering.

Figure 5:
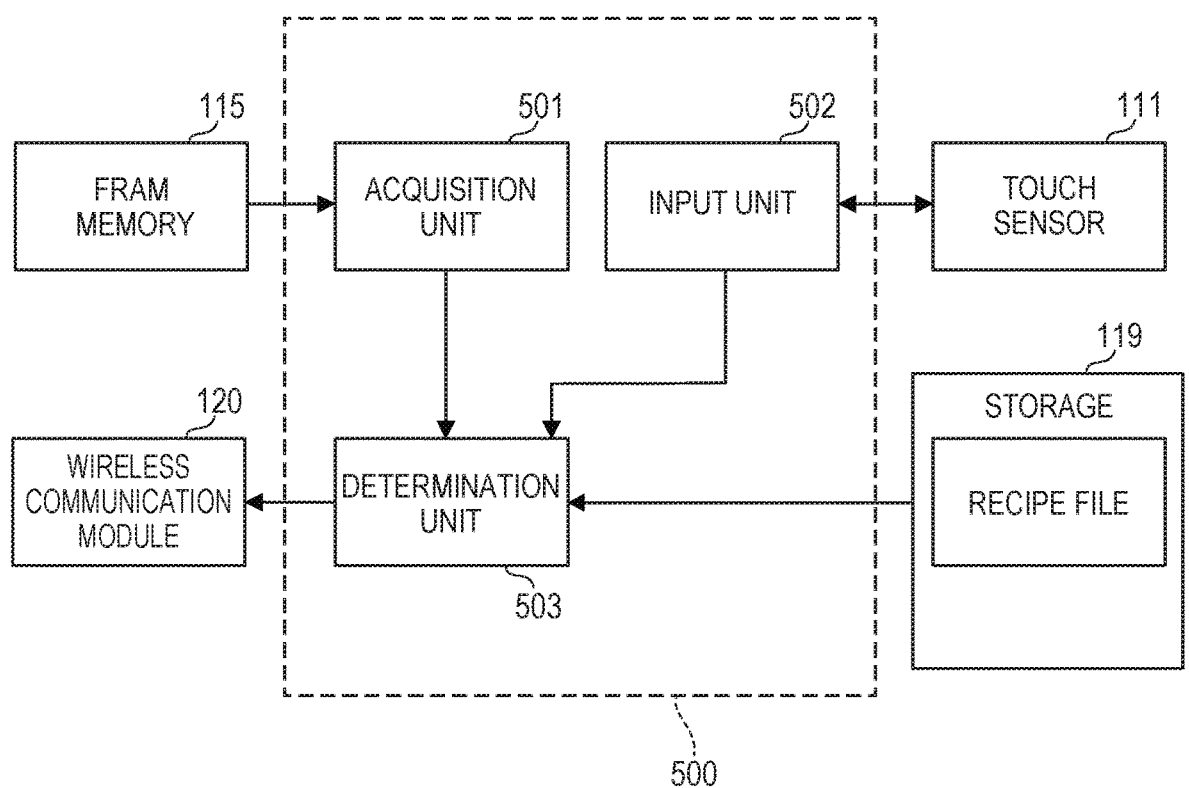
FIG. 5 is a function block diagram of an application program according to the first embodiment.

FIG. 5 is a function block diagram of a fragrance determination app 500 according to the present embodiment. The fragrance determination app 500 has an acquisition unit 501, an input unit 502, and a determination unit 503. The function of the fragrance determination app 500 is implemented by the CPU 116 reading and executing a program of the fragrance determination app 500 stored in the storage 119. That is, the CPU 116 functions as the acquisition unit 501, the input unit 502, and the determination unit 503 when the fragrance determination method is performed by the fragrance determination app 500.

The acquisition unit 501 can measure a physiological index of a human body based on image data stored in the frame memory 115. For example, the acquisition unit 501 can acquire heartbeat information such as a heart rate, a heartbeat interval, a heartbeat fluctuation, or the like by detecting a change in a color component between frames from image data of a plurality of frames obtained by capturing a fingertip of the user. The heartbeat information can also be acquired based on image data of another part of a human body such as a cheek, a palm, a face, or the like without being limited to a fingertip. Further, the physiological index may be another physiological index associated with an autonomic nerve (respiration, blood flow, body temperature, perspiration, or the like), an electroencephalogram, or the like without being limited to heartbeats. The physiological index may include blinks, motion of a head, or the like. For example, the acquisition unit 501 can recognize a contour position of a chest from image data by using image processing and acquire the number of times of respiration from movement of the chest. Similarly, the acquisition unit 501 can recognize the position of an eyebrow or a head from image data and acquire the number of blinks or the motion of the head. Further, the acquisition unit 501 may acquire a perspiration amount based on a signal from a sensor that detects an electric resistance of a skin.

Furthermore, the acquisition unit 501 calculates a psychosomatic state of the user from the measured physiological index. The psychosomatic state may include a stress state, a concentration state, or a sociality state. For example, the stress state is calculated based on heartbeat information and evaluated by three levels of low, middle, and high. The stress state may be evaluated based on fluctuations of heartbeats (pulse waves) or may be evaluated by a combination with another physiological index. Further, the concentration state is calculated based on the number of blinks or the frequency of motion of the head, for example. When the concentration state is high, the number of blinks tends to decrease, and the head tends to move less. The sociality state can be calculated from fluctuations of pulse waves. Here, the sociality can be expressed by flexibility or tolerance of mind.

The input unit 502 displays a user interface on the touchscreen 101 and inputs future information on a user selected on the user interface. The future information may include an action to be taken (a planned action) and a mood the user wants to be in (a desired mood). The planned action may be work, study, exercise, housework, dressing, at ease (rest), sleep, bathing, or the like. While the planned actions listed here are expected actions taken by the user itself in daily life, the planned action may be the detail of a care to be performed on the user in the future. For example, the planned action may be dressing, exercise, bathing, meal, rest, or sleep in a care site, the content of massage, counseling, or therapy in a medical site, an operation menu in a salon, or the like. The mood the user wants to be in may be a relaxed mood, a refreshing mood, a concentrating mood, a positive mood, a sociable mood, a feminine mood, or the like. For example, a list of planned actions is displayed as an icon on the user interface, and a planned action is selected by the user touching on the icon. The selected planned action is input to the input unit 502 from the touchscreen 101.

Similarly, the input unit 502 displays a user interface on the touchscreen 101 and inputs a mental state of the user selected on the user interface. For example, a list of mental states is displayed as an icon on the user interface. The mental state may be a bad state, a not-bad state, a good state, or the like. More specifically, a list indicating the detail of a concerned bad condition or the like may be displayed as an icon. A mental state is selected by the user touching on the icon, and the selected mental state is input to the input unit 502 from the touchscreen 101. Note that the entry method of a mental state is not limited to one using the touchscreen 101. For example, the user may acquire a mental state in advance by using a mentality question sheet (questionnaire) such as State-Trait Anxiety Inventory (STAI) and store the acquired mental state in the storage 119. The input unit 502 can read a mental state from the storage 119 instead of displaying the user interface.

The determination unit 503 determines a fragrance recipe in accordance with a psychosomatic state acquired by the acquisition unit 501 and future information and a mental state input by the input unit 502. The determination unit 503 can determine the fragrance recipe based on a recipe file stored in the storage 119. A plurality of fragrance recipes are included in the recipe file, and the determination unit 503 can select the optimal fragrance recipe from the plurality of fragrance recipes in accordance with a predetermined rule.

Figures 6, 7:
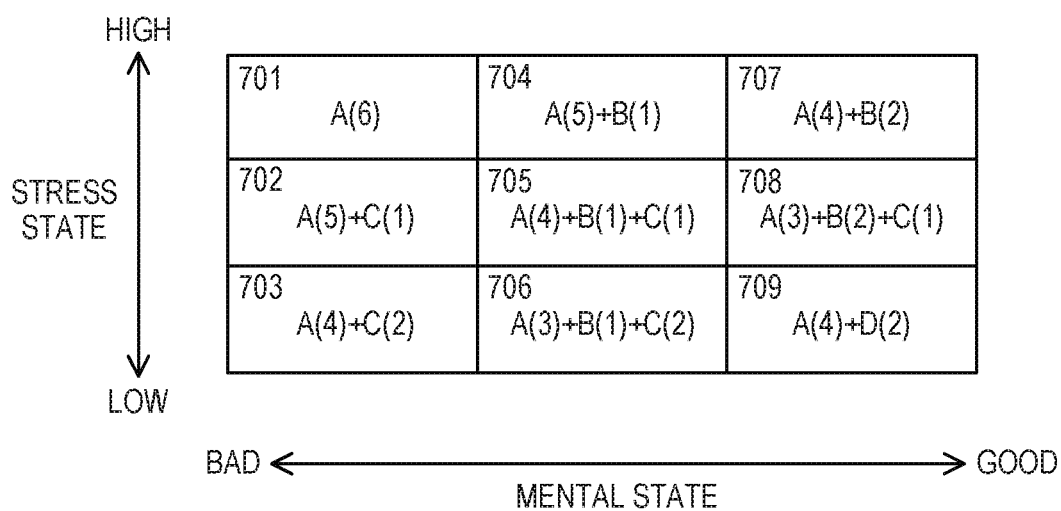
FIG. 6 is one example of the correspondence between a planned action and a note according to the first embodiment.
FIG. 7 is a diagram illustrating a fragrance recipe according to the first embodiment.

First, the determination unit 503 selects a main note of a fragrance recipe (type of fragrance) in accordance with a predetermined correspondence. Here, the note selected is the optimal note based on future information. That is, the user's mood is switched by the effect of a fragrance, and this note is much effective to cause the user to be in a mood suitable for a planned action or a mood the user wants to be in. As an example, FIG. 6 illustrates the correspondence between planned actions and notes. The notes A' to F' may be "fruity", "citrus", "floral", "soup", "green", "musk", "gourmand", "herbal", "aquatic", "woody", "oriental", "tea", "aldehydic", "minty", "aromatic", "spicy", "earthy", "mossy", "balsamic", "leather", "amber", or the like. Hereafter, perfumes having the notes A' to F' are referred to as perfumes A to F, respectively. Note that the correspondence between planned actions and notes and the correspondence between moods the user wants to be in and notes can be determined in advance by preparing perfumes of various notes and actually surveying a change of moods occurring before and after smelling a fragrance.

FIG. 7 illustrates fragrance recipes 701 to 709 in which the note A' illustrated in FIG. 6 is the main note. When selecting the note A' as a main note, the determination unit 503 selects one of the fragrance recipes 701 to 709. Each of the fragrance recipes describes the type and the mixing ratio of one or more perfumes. For example, according to the fragrance recipe 701, only the perfume A is used, and according to the fragrance recipe 702, the perfume A and the perfume C are mixed at a ratio of 5:1. According to the fragrance recipe 703, the perfume A and the perfume C are mixed at a ratio of 4:2, and according to the fragrance recipe 704, the perfume A and the perfume B are mixed at a ratio of 5:1. Further, according to the fragrance recipe 705, the perfume A, the perfume B, and the perfume C are mixed at a ratio of 4:1:1. Note that the types and mixing ratios of perfumes of the recipes 701 to 709 described here and a description method illustrated in FIG. 7 are mere examples, and the present invention is not limited thereto.

In FIG. 7, when a two-dimensional map in which the vertical axis represents the stress state and the horizontal axis represents the mental state is considered, the fragrance recipes 701 to 709 correspond to respective quadrants of the two-dimensional map. In all the fragrance recipes 701 to 709, the mixing ratio of the perfume A corresponding to the main note A' is the highest. The mixing ratio of the perfumes B to F (secondary perfume) that may be mixed with the perfume A (primary perfume) is changed in accordance with a stress state and a mental state. That is, according to the fragrance recipes 701 to 709, fragrances that are arranged with the notes B' to D' while the note A' is used as a basic note may be provided.

Figure 8:
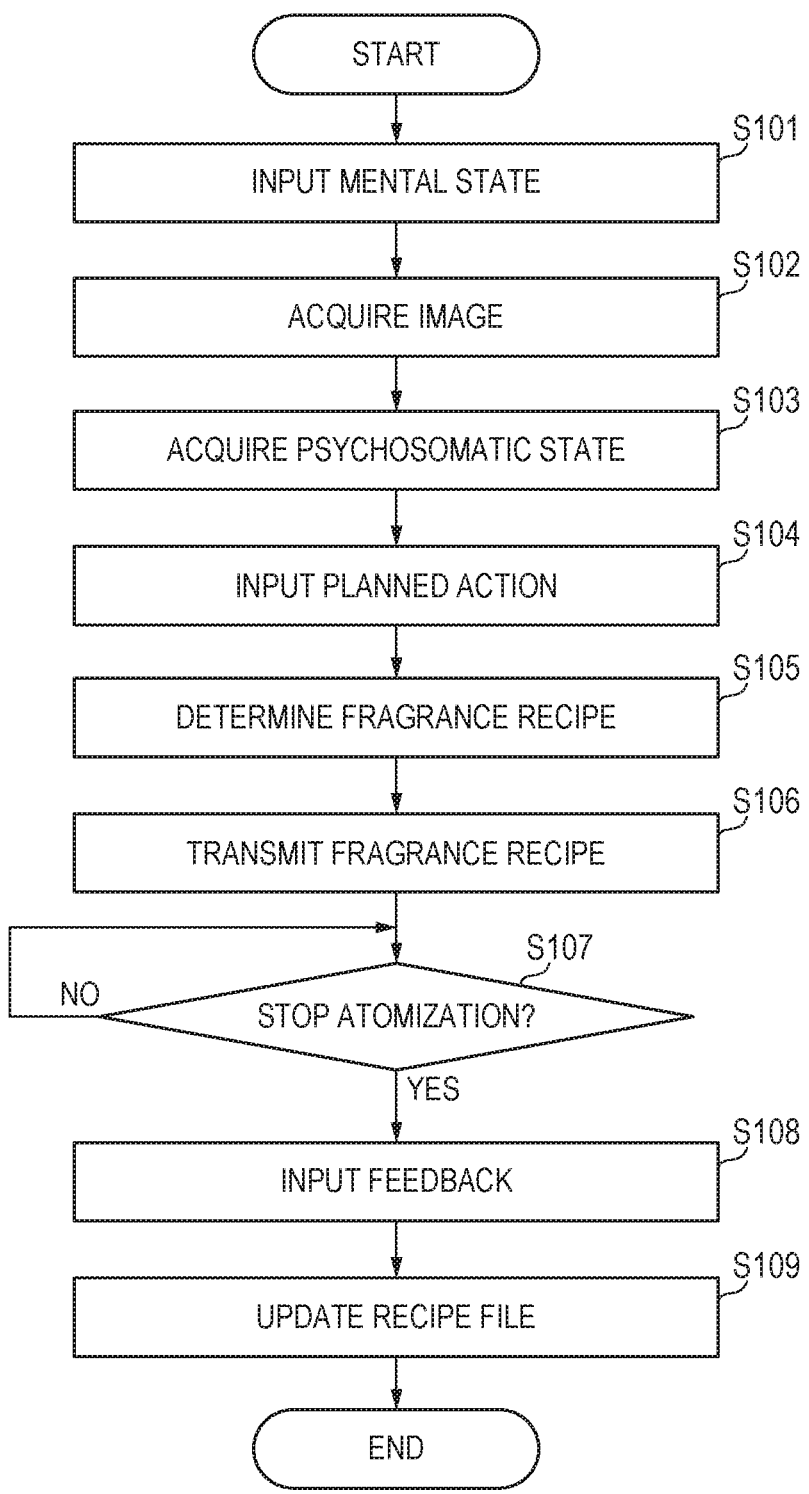
FIG. 8 is a flowchart illustrating a process in the mobile terminal according to the first embodiment.
Figure 9A:
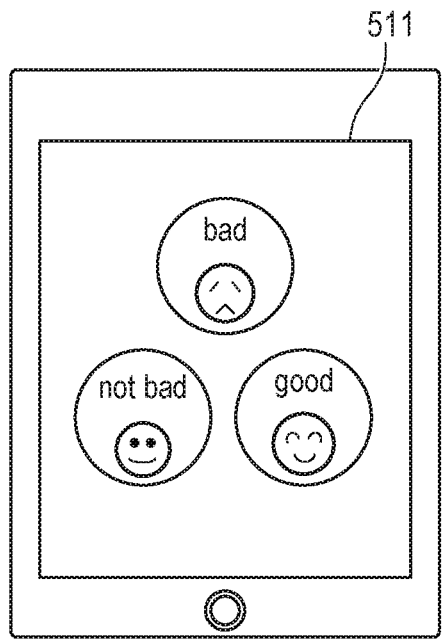
FIG. 9A is one example of a user interface of the mobile terminal according to the first embodiment.

FIG. 8 is a flowchart illustrating a process in the mobile terminal 100 according to the present embodiment. In the mobile terminal 100, once the user starts up the fragrance determination app 500, the CPU 116 displays, on the display 112, a user interface (UI) 511 used for inputting a mental state (step S101). On the UI 511, three icons that indicates mental states by three levels of "bad", "not bad", and "good" are displayed (FIG. 9A). The CPU 116 determines an icon selected by the user by detecting the position at which the user touches on the touch sensor 111. The CPU 116 stores the mental state indicated by the selected icon in the RAM 117.

Next, the CPU 116 acquires an image used for measuring a physiological index (step S102). For example, the CPU 116 displays a message such as "Please lightly press your fingertip on the lens of the camera", "Please do not move your fingertip until there is a signal", or the like on the display 112. The CPU 116 may display animation together with the message or may issue the massage with voice. In response to the user pressing its fingertip on the image capture unit 102 in accordance with the message, the CPU 116 causes the LED 103 to light and starts image capturing by the image capture unit 102. The CPU 116 performs image capturing at a predetermined framerate (for example, 60 frames per second) and stores image data of the fingertip in the frame memory 115.

Subsequently, the CPU 116 acquires a psychosomatic state based on the captured image data (step S103). For example, the CPU 116 detects heartbeat information from the image data of the fingertip and acquires a stress state based on the heartbeat information. Specifically, the CPU 116 averages values of an R (red) component in each frame and generates time series data of the averaged value of the R component. The CPU 116 then calculates the heart rate by performing frequency analysis on the time series data and calculating a peak of the spectrum. The heartbeat information is associated with a stress state, and the stress state is represented by three levels of low, middle, and high, for example. For example, when the heart rate is higher than or equal to a predetermined threshold, the CPU 116 evaluates the stress state to be "high".

Figure 9B:
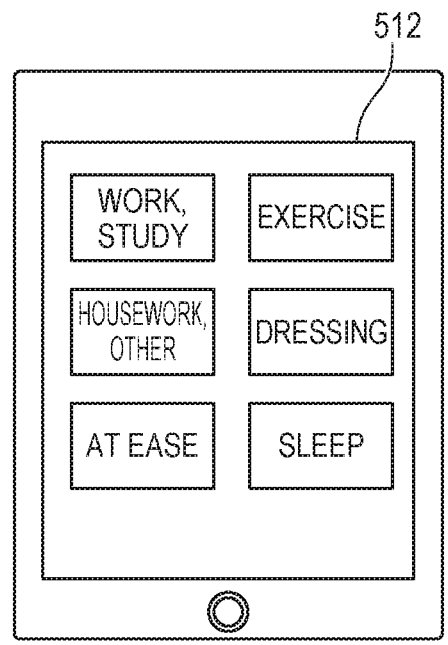
FIG. 9B is one example of a user interface of the mobile terminal according to the first embodiment.

Next, the CPU 116 displays, on the display 112, a UI 512 used for inputting a planned action (step S104). The UI 512 displays six icons indicating "concentrate for work or study", "do exercise or light exercise", "housework, others", "dress before outing", "be at ease (take a rest)", and "sleep", for example (FIG. 9B). The CPU 116 determines an icon selected by the user by detecting the position at which the user touches on the touch sensor 111. The CPU 116 stores the planned action indicated by the selected icon in the RAM 117. Note that steps S101 to S104 may be performed in any process order.

The CPU 116 determines a fragrance recipe based on the mental state, the stress state, and the planned action that have been obtained so far (step S105). First, the CPU 116 selects a note corresponding to the planned action from the correspondence illustrated in FIG. 6. For example, when the planned action is "work, study", the CPU 116 selects the note A'. Next, the CPU 116 selects a fragrance recipe in accordance with the mental state and the stress state out of the fragrance recipes 701 to 709 associated with the note A' illustrated in FIG. 7. For example, when the mental state is bad and the stress state is low, the CPU 116 selects the fragrance recipe 703. The CPU 116 stores the selected fragrance recipe in the storage 119 together with the mental state, the stress state, and the planned action used for selection of the fragrance recipe.

Figure 9C:
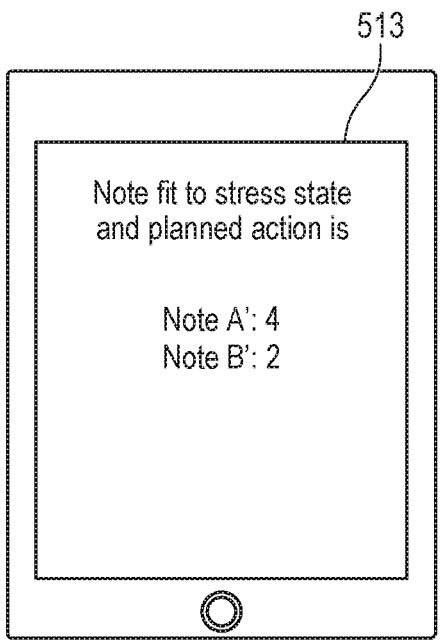
FIG. 9C is one example of a user interface of the mobile terminal according to the first embodiment.

Furthermore, the CPU 116 displays, on the display 112, a UI 513 used for providing the detail of the selected fragrance recipe to the user. For example, when the fragrance recipe 703 is selected, the UI 513 displays that the mixing ratio of a perfume having the note A' and a perfume having the note B' is 4:2 (FIG. 9C).

Next, the CPU 116 establishes the wireless communication 300 with the fragrance generation device 200 by using the wireless communication module 120 and transmits the selected fragrance recipe to the fragrance generation device 200 (step S106). For example, when the fragrance recipe 708 is selected, the CPU 116 transmits the types of perfumes, namely, A, B, and C and the mixing ratio thereof, namely, 3:2:1 to the fragrance generation device 200. Note that the CPU 116 may pre-store a recipe file in the fragrance generation device 200 and transmit only the identification number (ID) of the fragrance recipe.

After the fragrance recipe is transmitted, atomization of the perfume is started at the fragrance generation device 200. The CPU 116 determines whether or not there is an instruction from the user to stop atomization (step S107). The user may provide an instruction to stop atomization by touching on a stop icon displayed on the UI, for example. If there is no instruction to stop atomization (step S107, NO), the CPU 116 stands by until an instruction to stop atomization is issued. The CPU 116 may set a timer (for example, two to three hours) and proceed to the next process (step S108) after the set time has elapsed. If there is an instruction to stop atomization (step S107, YES), the CPU 116 transmits a command to stop atomization to the fragrance generation device 200 via the wireless communication 300.

Figure 9D:
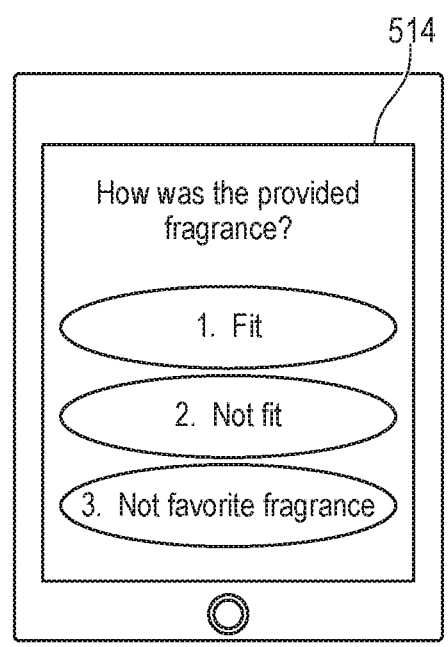
FIG. 9D is one example of a user interface of the mobile terminal according to the first embodiment.

Furthermore, the CPU 116 displays, on the display 112, a UI 514 used for inputting a feedback from the user (step S108). For example, the UI 514 displays three choices of "fragrance is fit", "fragrance is not fit", and "not favorite fragrance" (FIG. 9D), and the user selects a suitable one from these choices. Further, the CPU 116 may feed back a measurement result of the physiological index. For example, the CPU 116 may again measure a physiological index used in the determination of the fragrance recipe and feed back a change of the measurement values resulted before and after the fragrance is provided. The CPU 116 stores such a feedback from the user in the storage 119.

Finally, the CPU 116 updates a recipe file based on the feedback from the user (step S109). For example, when receiving a feedback of "fragrance is not fit" for the fragrance recipe 703, the CPU 116 changes the recipe to any one of the fragrance recipes 702, 705, and 706 (see FIG. 7) similar to the fragrance recipe 703. Further, when receiving a feedback of "not favorite fragrance" for the fragrance recipe 701, the CPU 116 performs subsequent selection from fragrance recipes which do not contain the perfume A of the fragrance recipe 701. Note that, while an example in which a planned action is input as future information has been described in the illustration of the above flowchart, the same process can be performed also when a mood the user wants to be in is input.

Figure 10:
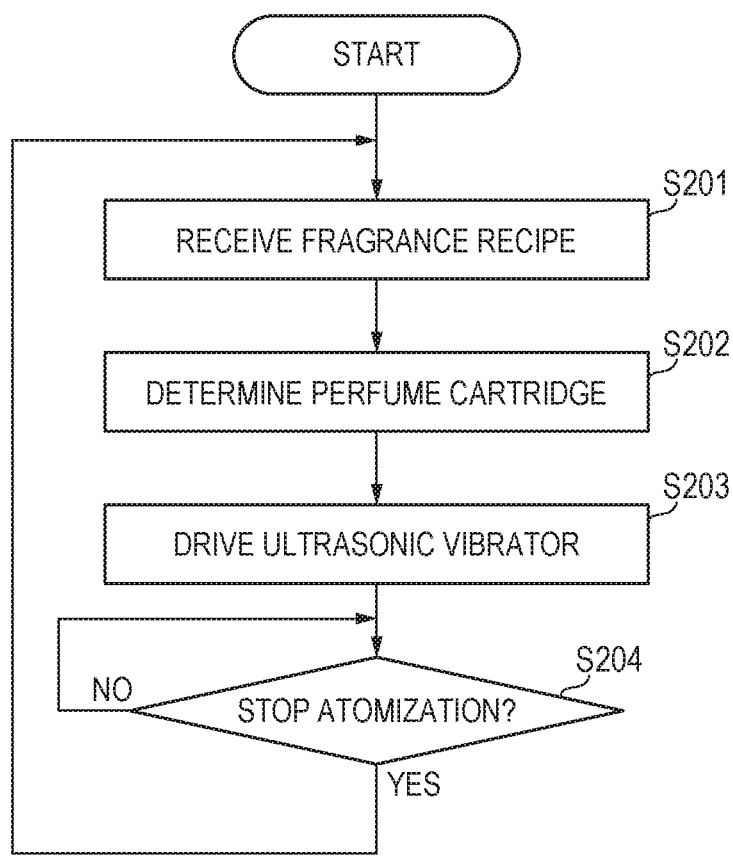
FIG. 10 is a flowchart illustrating a process in the fragrance generation device according to the first embodiment.

FIG. 10 is a flowchart illustrating a process in the fragrance generation device 200 according to the present embodiment. First, the control unit 208 receives a fragrance recipe from the mobile terminal 100 via the wireless communication module 209 (step S201). Subsequently, the control unit 208 acquires the type and the mixing ratio of perfumes from the received fragrance recipe and determines the perfume cartridge 201 as one or more drive targets and intermittent time (step S202). The intermittent time describes a timing of atomization when turning on and off of atomization is repeated. For example, when the perfume A and perfume B are mixed at 5:1, the perfume cartridge 201a containing the perfume A and the perfume cartridge 201b containing the perfume B are determined as the drive targets. Further, for example, the intermittent cycle of atomization is set at 5 seconds, and it is determined that the atomization from the perfume cartridge 201a is performed during 0 to 5 seconds within an intermittent cycle (always ON) and the atomization from the perfume cartridge 201b is performed during 0 to 1 second within the intermittent cycle.

Next, the control unit 208 transmits a signal based on the determined drive target and an atomization period to the drive circuit 205. In response to a signal from the control unit 208, voltages are applied from the drive circuit 205 to the ultrasonic vibrator 204a of the perfume cartridge 201a and the ultrasonic vibrator 204b of the perfume cartridge 201b, respectively (step S202). Thereby, the perfume mixed in accordance with the fragrance recipe is atomized from the perfume cartridges 201a and 201b.

During atomization of the perfume being performed, the control unit 208 determines whether or not a command to stop atomization is received from the mobile terminal 100 (step S204). If no command to stop atomization is received (step S204, NO), the control unit 208 stands by until the command is received. If the command to stop atomization is received (step S204, YES), the control unit 208 stops driving the ultrasonic vibrator 204. The control unit 208 then returns to the initial step of the flowchart and stands by until a new fragrance recipe is received.

In the present embodiment, a fragrance recipe is determined based on information such as a psychosomatic state of a user such as a stress state, an action to be next taken by the user, a mood the user wants to be in, or the like. That is, since a fragrance recipe is determined by taking a living scene from the current state to a future action of the user into consideration, the provided fragrance can switch the user's mood to a suitable preference. For example, when it is assumed that the user is going to bed, the effect of a fragrance will be different in accordance with the current stress state. According to the present embodiment, it is possible to provide the optimal fragrance in accordance with various living scenes.

Second Embodiment

Figure 11:
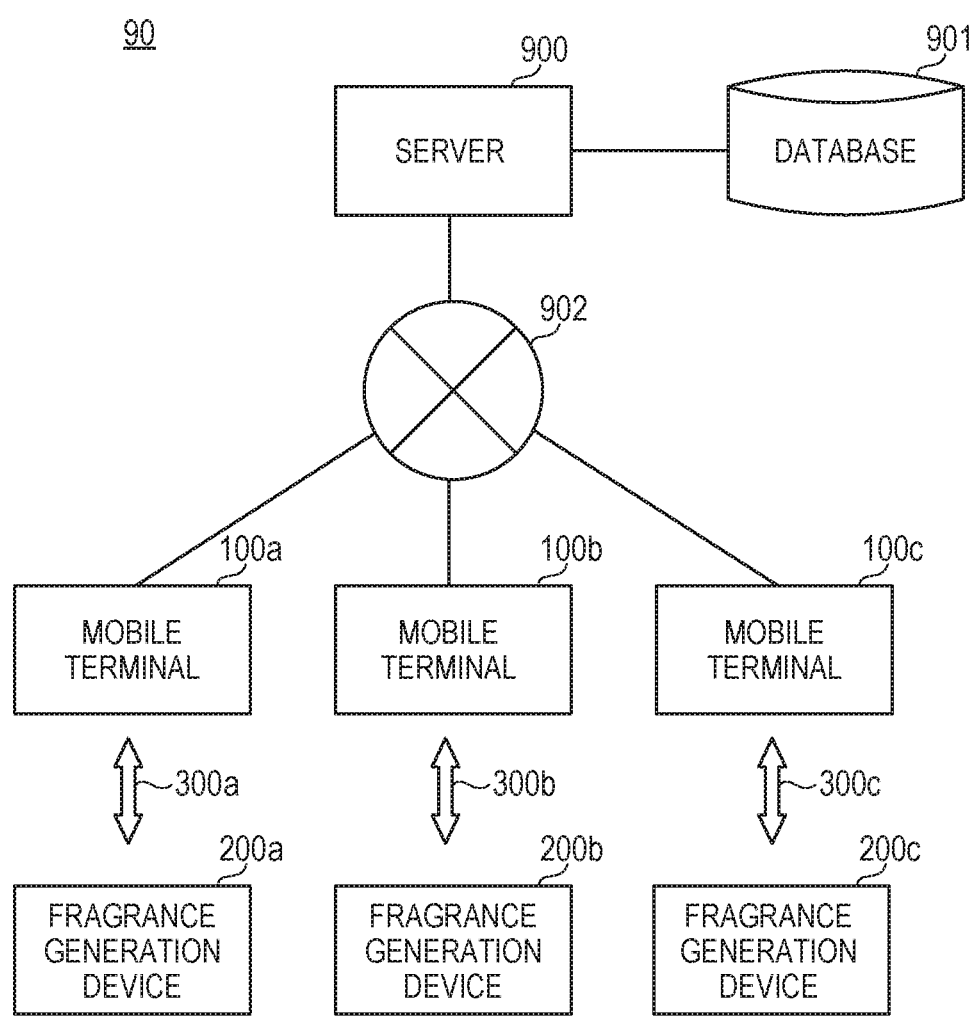
FIG. 11 is a schematic diagram of a fragrance generation system according to a second embodiment.

Next, a fragrance generation system 90 according to a second embodiment of the present invention will be described. FIG. 11 is a block diagram of the fragrance generation system 90 according to the present embodiment. The fragrance generation system 90 has mobile terminals 100a to 100c, fragrance generation devices 200a to 200c, a server 900, a database 901, and a network 902. Since the mobile terminals 100a to 100c and the fragrance generation devices 200a to 200c are configured in the same manner as the mobile terminal 100 and the fragrance generation device 200 according to the first embodiment, respectively, features different from those in the first embodiment will be mainly described. In the fragrance generation system 90, feedbacks of users acquired by the mobile terminals 100a to 100c are stored in the database 901 connected to the server 900.

The mobile terminals 100a to 100c and the fragrance generation devices 200a to 200c are connected through the wireless communications 300a to 300c, respectively. Further, the mobile terminals 100a to 100c and the server 900 are communicably connected via the network 902 such as a mobile communication network, the internet, or the like. Each of wireless communication modules 120a to 120c of the mobile terminals 100a to 100c can be connected to the network 902 by using a mobile communication scheme such as Long Term Evolution (LTE), 4th Generation (4G), or the like. Note that the fragrance generation system 90 may include more mobile terminals 100 without limited to the mobile terminals 100a to 100c.

The server 900 has a CPU, a memory, a communication interface, and the like and manages the fragrance generation system 90. The server 900 has a function of downloading the fragrance determination app 500 to the mobile terminals 100a to 100c, a function of collecting feedbacks from the mobile terminals 100a to 100c, and a function of creating and updating a recipe file, for example. The database 901 is a storage device such as a hard disk and stores feedbacks from the mobile terminals 100a to 100c, recipe files, or the like. The recipe file may be a shared file used by the mobile terminals 100a to 100c or may be a separate file created for each of the mobile terminals 100a to 100c (each user).

Figure 12:
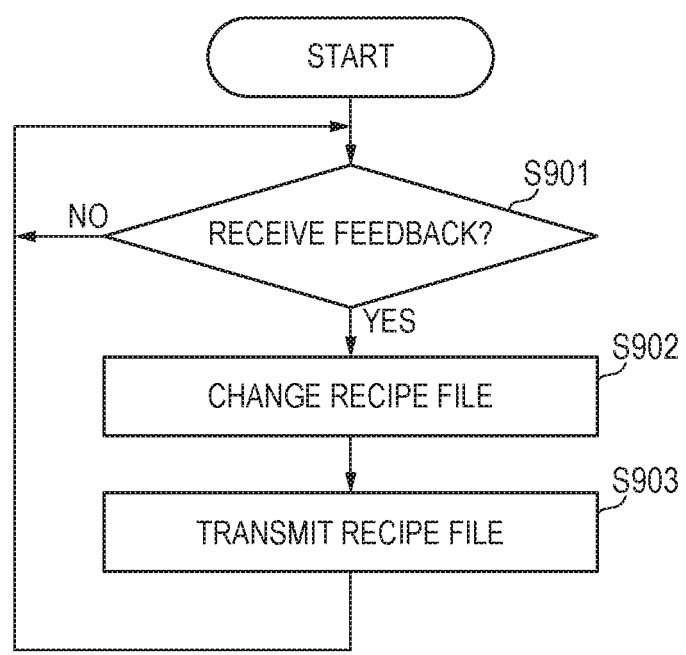
FIG. 12 is a flowchart illustrating a process in a server according to the second embodiment.

FIG. 12 is a flowchart illustrating a process in the server 900 according to the present embodiment. First, the server 900 determines whether or not a feedback is received from any of the mobile terminals 100a to 100c (step S901). If no feedback is received (step S901, NO), the server 900 stands by until a feedback is received from any of the mobile terminals 100a to 100c. If a feedback is received (step S901, YES), the server 900 changes the recipe file based on the received feedback (step S902).

For example, the server 900 collects a feedback on a fragrance recipe basis and changes a fragrance recipe for which a feedback of "fragrance is not fit" is received at a predetermined rate or higher. A method of changing a fragrance recipe may be the same as the process of step S109 described above. Further, the server 900 may manage recipe files on a user basis and change the fragrance recipe based on a feedback of another user. For example, when a fragrance recipe is changed, a fragrance recipe receiving high evaluation of feedbacks from others may be preferentially selected.

Next, the server 900 transmits the changed recipe file to the mobile terminals 100a to 100c (step S903). When recipe files are managed on a user basis, a recipe file is transmitted to only the mobile terminal of a target user of the recipe file. In response to the recipe file being received at the mobile terminals 100a to 100c, the detail of the change of the fragrance recipe is displayed. The server 900 returns to step S901 and stands by for a new feedback.

Modified Embodiments

The embodiments described above illustrate mere embodied examples in implementing the present invention, and the technical scope of the present invention is not construed in a limiting sense by the above. That is, the present invention is not limited to the embodiments described above and can be changed within the scope not departing from the spirit of the present invention.

For example, the mobile terminal 100 may determine the mental state (mood) of the user by acquiring an image, a voice, or other physiological indexes. For example, the mental state of the user may be determined by capturing a face of the user and analyzing an expression of the face by using image processing, instead of causing the user to select an icon. Further, the physiological index of a user may be acquired by the fragrance generation device 200. For example, a contact-type heartbeat sensor may be provided in the handle 203, and heartbeats may be automatically measured when the user carries the fragrance generation device 200.

Further, the mobile terminal 100 may determine a fragrance recipe based on an action pattern, a biorhythm of a user, or the like. For example, an action pattern or a biorhythm can be analyzed based on the time when a planned action or a physiological index is acquired. Furthermore, the mobile terminal 100 may determine a lighting pattern, a BGM, or the like in the same manner as a fragrance recipe. In the fragrance generation device 200, switching of moods can be more effectively performed by providing lighting or a music to the user together with a fragrance.

The scope of each of the example embodiments described above further includes a processing method that stores, in a storage medium, a program that causes the configuration of each of the example embodiments to operate so as to implement the function of each of the example embodiments described above (for example, the fragrance determination app), reads the program stored in the storage medium as a code, and executes the program in a computer. That is, the scope of each of the example embodiments described above also includes a computer readable storage medium. Further, each of the example embodiments described above includes not only the storage medium in which the program is stored but also the program itself.

As the storage medium, for example, a floppy (registered trademark) disk, a hard disk, an optical disk, a magneto-optical disk, a CD-ROM, a magnetic tape, a nonvolatile memory card, or a ROM can be used. Further, the scope of each of the example embodiments described above includes an example that performs a process in cooperation with another software or a function of an add-in board without being limited to an example that performs a process by an individual program stored in the storage medium.

REFERENCE SIGNS LIST 100 mobile terminal
101 touchscreen
102 image capture unit
116 CPU
117 RAM
118 ROM
119 storage
120 wireless communication module
200 fragrance generation device
201 perfume cartridge
204 ultrasonic vibrator
208 control unit
209 wireless communication module
300 wireless communication
500 application program
511 to 514 user interface
701 to 709 fragrance recipe
900 server
901 database

The invention claimed is:

1. A mobile terminal comprising:
an acquisition unit configured to acquire a psychosomatic state from a physiological index of a user;
an input unit configured to input at least one of a planned action or a desired mood of the user;
a determination unit configured to determine a recipe out of one or more recipes including one or more types of one or more perfumes and one or more mixing ratios of the one or more perfumes based on the psychosomatic state and the at least one of the planned action or the desired mood; and
a communication unit configured to transmit the determined recipe to a fragrance generation device.

2. The mobile terminal according to claim 1, wherein the input unit is further configured to input a current mental state of the user, and the determination unit determines the recipe out of the one or more recipes based on the mental state when the input unit inputs the current mental state of the user.

3. The mobile terminal according to claim 2, wherein the mental state includes a first mood or a second mood.

4. The mobile terminal according to claim 1, wherein the determination unit determines, among the one or more perfumes, a primary perfume of a highest mixing ratio of the one or more mixing ratios based on the at least one of the planned action or the desired mood and determines, among the one or more perfumes, a secondary perfume of a lower mixing ratio than the primary perfume based on the psychosomatic state.

5. The mobile terminal according to claim 1, wherein the physiological index includes at least one of heartbeats, blinks, or motion of a head.

6. The mobile terminal according to claim 1, wherein the psychosomatic state includes at least one of a stress state, a concentration state, or a sociality state.

7. The mobile terminal according to claim 1, wherein the planned action is one of work, study, exercise, housework, dressing, rest, sleep, or bathing.

8. The mobile terminal according to claim 1, wherein when the input unit inputs the desired mood of the user, the determination unit determines the recipe out of the one or more recipes based on the desired mood, and
wherein when the input unit inputs the planned action of the user, the determination unit determines the recipe out of the one or more recipes based on the planned action.

9. The mobile terminal according to claim 1, wherein the acquisition unit calculates the physiological index by using image data of the user.

10. The mobile terminal according to claim 1, wherein the determination unit selects the recipe from the one or more recipes in accordance with a predetermined rule, wherein the predetermined rule includes at least one of a predetermined correspondence between the planned action and the one or more types of the one or more perfumes or a predetermined correspondence between the desired mood and the one or more types of the one or more perfumes.

11. The mobile terminal according to claim 10, wherein the input unit is further configured to input feedback from the user with respect to the determined recipe.

12. The mobile terminal according to claim 11, wherein the determination unit updates the predetermined rule based on the feedback.

13. A server, comprising a processor configured to communicate with the mobile terminal according to claim 11, wherein the processor of the server updates the predetermined rule based on the feedback from a plurality of users with respect to the determined recipe.

14. The mobile terminal according to claim 1, wherein the recipe out of the one or more recipes includes a perfume, among the one or more perfumes, having at least one note of fruity, citrus, floral, soup, green, musk, gourmand, herbal, aquatic, woody, oriental, tea, aldehydic, minty, aromatic, spicy, earthy, mossy, balsamic, leather, or amber.

15. A mobile terminal comprising:
   an acquisition unit configured to acquire a psychosomatic state from a physiological index of a user, which is calculated by using image data of the user;
   an input unit configured to input at least one of a planned action or a desired mood of the user;
   a determination unit configured to determine a recipe out of one or more recipes including one or more types of one or more perfumes and one or more mixing ratios of the one or more perfumes based on the psychosomatic state and the at least one of the planned action or the desired mood;
   a communication unit configured to transmit the determined recipe to a fragrance generation device; and
   an image capture unit configured to perform capturing of the image data.

16. A fragrance determination method comprising steps of:
   acquiring, by a processor, a psychosomatic state from a physiological index of a user;
   inputting, by the processor, at least one of a planned action or a desired mood of the user;
   determining, by the processor, a recipe out of one or more recipes including one or more types of one or more perfumes and one or more mixing ratios of the one or more perfumes based on the psychosomatic state and the at least one of the planned action or the desired mood; and
   generating, by a fragrance generation device, a fragrance based on the determined recipe.

17. A non-transitory storage medium in which a program is stored, wherein the program causes the processor to execute each step of the fragrance determination method according to claim 16.

18. A fragrance generation device, comprising a processor configured to perform the steps of a fragrance determination method comprising:
   acquiring, by the processor, a psychosomatic state from a physiological index of a user;
   inputting, by the processor, at least one of a planned action or a desired mood of the user;
   determining, by the processor, a recipe out of one or more recipes including one or more types of one or more perfumes and one or more mixing ratios of the one or more perfumes based on the psychosomatic state and the at least one of the planned action or the desired mood; and
   generating, by the fragrance generation device, a fragrance based on the determined recipe,
   wherein the fragrance generation device atomizes a perfume, among the one or more perfumes, based on the determined recipe.

* * * * *